(12) United States Patent
Wages et al.

(10) Patent No.: US 6,394,141 B2
(45) Date of Patent: May 28, 2002

(54) SINGLE LUMEN TO MULTIPLE LUMEN TRANSITION CATHETER AND METHOD

(75) Inventors: Christopher Mason Wages, San Miguel, CA (US); David Batdorf, Jr., Elk Rapids, MI (US); Charles Schryver, Atascadero, CA (US)

(73) Assignee: Specialty Silicone Fabricators, Inc., Paso Robles, CA (US)

( * ) Notice: Subject to any disclaimer, the term of this patent is extended or adjusted under 35 U.S.C. 154(b) by 0 days.

(21) Appl. No.: 09/731,458

(22) Filed: May 18, 2001

Related U.S. Application Data

(63) Continuation-in-part of application No. 09/492,907, filed on Jan. 27, 2000, now abandoned, which is a continuation-in-part of application No. 09/131,487, filed on Aug. 10, 1998, now abandoned.

(51) Int. Cl.⁷ ............................. F16L 11/22; A61M 5/00
(52) U.S. Cl. ...................... 138/115; 138/116; 138/177; 604/43
(58) Field of Search ................................ 138/115, 116, 138/117, 177, 178, 43; 604/280

(56) References Cited

U.S. PATENT DOCUMENTS

| | | | | |
|---|---|---|---|---|
| 2,086,654 A | * | 7/1937 | Winder ..................... | 138/115 X |
| 2,122,335 A | * | 6/1938 | Berman et al. ......... | 138/115 X |
| 2,663,325 A | * | 12/1953 | Bede ....................... | 138/115 X |
| 5,053,023 A | * | 10/1991 | Martin ....................... | 604/280 |
| 5,057,073 A | * | 10/1991 | Martin ......................... | 604/43 |
| 5,219,335 A | * | 6/1993 | Willard et al. .............. | 604/164 |
| 5,221,256 A | * | 6/1993 | Mahurkar .................... | 604/43 |

\* cited by examiner

Primary Examiner—Patrick Brinson
(74) Attorney, Agent, or Firm—Michael G. Petit

(57) ABSTRACT

A tubing having unitary construction and having a single lumen portion, a multilumen portion and a transition portion therebetween. The single lumen is in fluid communication with each and every lumen comprising the multilumen portion. The tubing may be made in any desired length by means of extrusion. The outer surface of the tubing may be either smooth or grooved and have any desired cross-sectional geometry. Similarly, any of the lumens can be made to have a desired cross-sectional shape and size. Although the tubing can be made from any extrudable material, a preferred material is medical grade silicone clastomer. An extrusion apparatus and a method for making the tubing in a continuous process is described.

3 Claims, 5 Drawing Sheets

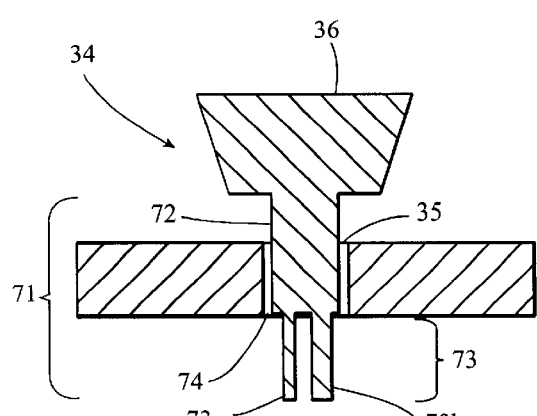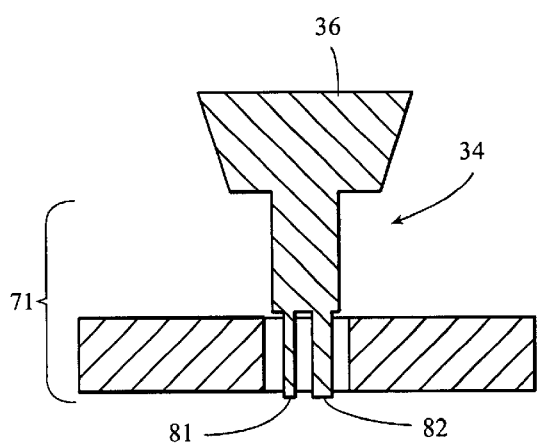
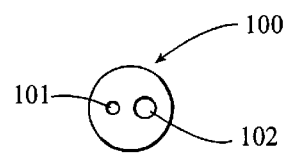
Figure 9  Figure 10
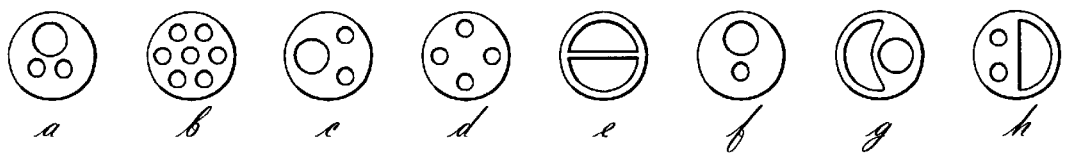
Figure 11
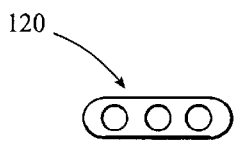 
Figure 12  Figure 13
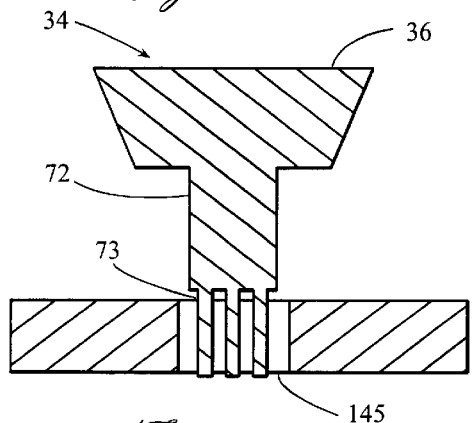 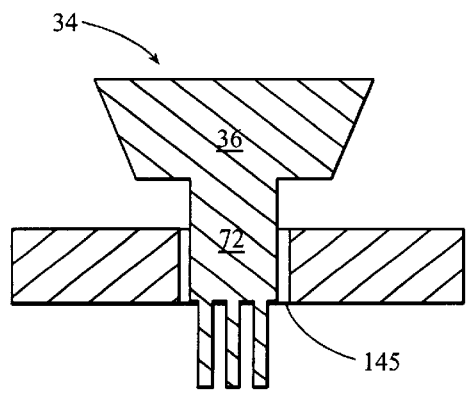
Figure 14  Figure 15

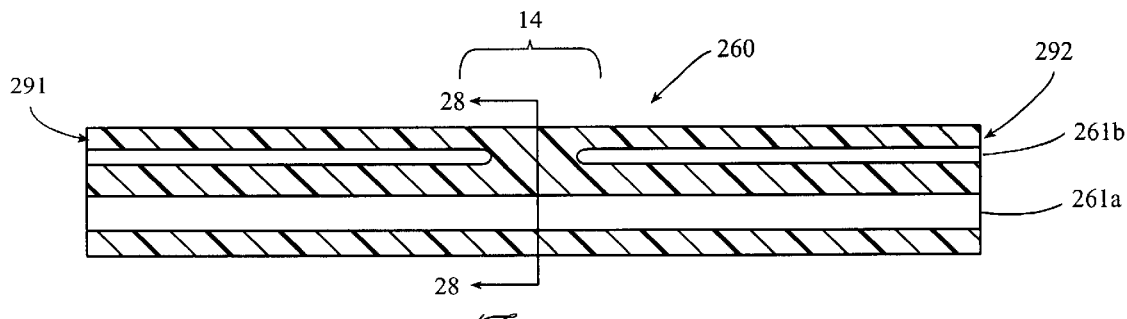
Figure 29
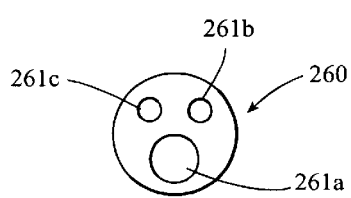
Figure 30
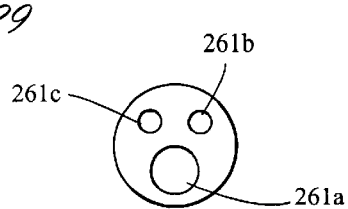
Figure 31
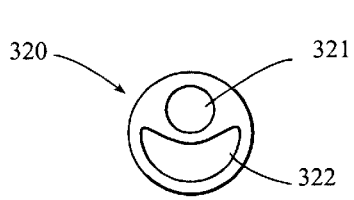
32a
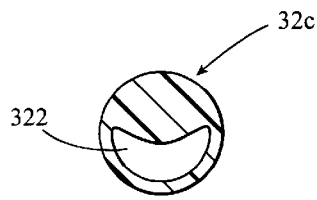
32d
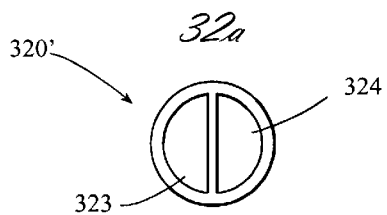
32b
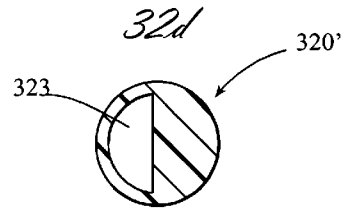
32e
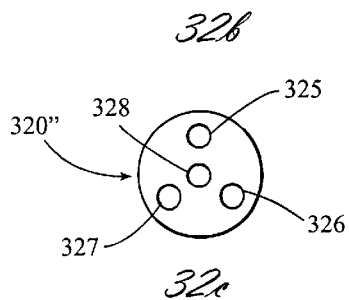
32c
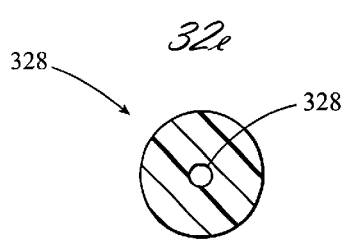
32f
Figure 32

SINGLE LUMEN TO MULTIPLE LUMEN TRANSITION CATHETER AND METHOD

CROSS REFERENCE TO RELATED APPLICATIONS

This is a continuation-in-part division of application Ser. No. 09/492,907; filed Jan. 27, 2000, now abandoned, which is a continuation-in-part of Ser. No. 09/131,487, filed Aug. 10, 1998, now abandoned.

BACKGROUND OF THE INVENTION

1. Field of the Invention

A multilumen tubing, and more particularly, a tubing having a multilumen portion in fluid communication with a single lumen portion and having unitary construction.

2. Prior Art

A variety of multilumen catheters and similar tubing is well established in the prior art. Chee, et al., in U.S. Pat. No. 5,542,937, discloses a multilumen catheter made by an extrusion process wherein the lumens are coextensive with the length of the catheter. Means for changing the composition of the clastomer comprising the catheter body during the extruded elongation of the catheter is discussed.

Miller et al., in U.S. Pat. No. 5,683,640, discloses a dual lumen catheter wherein a first lumen is coextensive with the length of the catheter and a second lumen, parallel to the first lumen, is shorter than the first lumen and exits the catheter via a port in the catheter wall. A hollow hub is affixed to one end of the catheter and is in fluid communication with both the first and second lumen. Medical applications of the catheter include infusion of fluids and peritoneal dialysis.

Multilumen catheters, wherein one lumen is in fluid communication with a second lumen within the body of the catheter, are known in the art. For example, Willard et al., in U.S. Pat. No. 5,219,335, discloses an intravascular introducer sheath having two lumens. An axial lumen is coextensive with the body of the sheath and dimensioned to accommodate an introducer wire therewithin; the introducer wire being of the type commonly employed for inserting a catheter in a blood vessel. In this procedure, a wire is threaded through an excision in the skin and advanced through a blood vessel until the end of the wire is in a predetermined location within the vascular system. The distal end of the axial lumen of the introducer sheath is placed over the proximal (accessible) end of the wire and advanced along the wire until the introducer sheath is in position. The wire is then withdrawn and a suitable device, such as a stent disposed on the outer surface of a catheter, is advanced through the axial lumen of the introducer sheath until the device is correctly positioned within the blood vessel. The introducer sheath is then removed. After deployment of the device, the catheter may be removed.

The axial lumen in such introducer sheaths, through which the guidewire passes, is straight. This construction, (i.e., a straight axial lumen) permits facile passage of the introducer sheath over the guidewire. Willard et al.'s introducer sheath has a second lumen that is parallel to the axial lumen. A connection providing fluid communication between the second lumen and the axial lumen is disposed near the distal end of the introducer sheath. Inasmuch as the axial lumen is straight, the second lumen is bent at the interluminal connection rendering the juncture between the two lumens asymmetric. For the purpose of an introducer sheath, a catheter having a tubular body portion with a straight axial lumen and an asymmetric, abruptly bent second lumen is acceptable and perhaps even essential. For other applications, however, such as the use of a single to multilumen catheter for transporting fluids, the asymmetric abrupt bend in the transition portion comprised of the connection can produce unwanted turbulence at the juncture of two fluid streams. It is, therefore, desirable to provide a single to multilumen catheter wherein the transition portion forming the connection between the single lumen and multilumen portion of the catheter is both smooth and symmetric.

The attachment of a hub to a multilumen tubing, or any tubing, compromises the structural integrity of the assembly. Either axial or lateral tension on the hub may cause it to separate from the catheter. This problem can be overcome. by providing a multilumen catheter having unitary construction, wherein multiple lumens, terminating at one end of a catheter, are in fluid communication with a single lumen terminating at the opposing end of the catheter.

SUMMARY OF THE INVENTION

It is a first object of the invention to provide a unitary tubing having a multilumen end and a single lumen end wherein fluid communication between the single lumen and the multiple lumens is established by means of a transition portion disposed therebetween.

It is a further object of the invention to provide a unitary tubing meeting the above objectives and wherein the unitary tubing has a uniform outer diameter along the entire length thereof.

It is still another object of the present invention to provide a unitary tubing meeting the above objectives wherein the transition portion disposed between the single lumen and multiple lumen portions of the tubing is symmetric with respect to an axis defined by the direction defined by the single lumen.

It is another object of the invention to provide a medical catheter meeting the above-stated objective in any desired length and diameter.

It is still a further object of the invention to provide an apparatus and method for making a multilumen tubing meeting the objectives stated above.

The features of the invention believed to be novel arc set forth with particularity in the appended claims. However the invention itself, both as to organization and method of operation, together with further objects and advantages thereof may be best be understood by reference to the following description taken in conjunction with the accompanying drawings in which:

BRIEF DESCRIPTION OF THE DRAWINGS

FIG. 7 is a cross-sectional view of a portion of an extruder die showing an outlet aperture and mandrel in accordance with the invention, wherein the mandrel includes a cylindrical upper portion and a configured lower portion with the upper cylindrical portion of the mandrel partially obstructing the extruder's outlet aperture.

FIG. 8 illustrates the relationship between the mandrel and outlet aperture within the extruder die of FIG. 7 with the lower configured portion of the mandrel partially obstructing the outlet aperture.

FIG. 9 is an end view of a portion of tubing extruded when the upper portion of a mandrel is cylindrical and partially obstructs the extruder's outlet aperture as illustrated in FIG. 7.

FIG. 10 is an end view of a portion of tubing extruded when the lower portion of a mandrel is comprised of two cylindrical pins which partially obstruct the extruder's outlet aperture as illustrated in FIG. 8

FIGS. 11a–h are a series of end views of a tubing extruded when the configured lower portion of a mandrel is partially obstructs the extruder's outlet aperture as illustrated in FIG. 8 illustrating a variety of multilumen configurations corresponding to various configurations of the lower mandrel.

FIG. 12 is an end view of a triple lumen tubing extruded through a die with the mandrel positioned as shown in FIG. 8, wherein both the outlet aperture and the upper portion of the mandrel are oval and the lower configured portion of the mandrel comprises three cylindrical pins affixed to the upper portion.

FIG. 13 is an opposing end view of a single lumen portion of the triple lumen tubing shown in FIG. 12, extruded when the upper oval portion of the mandrel partially obstructs the oval outlet aperture as shown in FIGS. 7.

FIG. 14 is a cross-sectional view of a portion of the extruder die illustrating the position of the mandrel within the outlet aperture during extrusion of the triple lumen portion of the tubing shown in FIG. 12.

FIG. 15 is a cross-sectional view of a portion of the extruder die illustrating the position of the mandrel within the outlet aperture during extrusion of the single lumen portion of the tubing shown in FIG. 12.

FIG. 29 is a cross-sectional view of a length of triple-lumen transition tubing, viewed along section line 29—29 of FIG. 26, which has been extruded through an extrusion die in accordance with FIGS. 24 and 27 in a continuous extrusion process.

FIG. 30 is a proximal end view of the length of triple-lumen transition tubing shown in FIG. 29.

FIG. 31 is a distal end view of the length of triple-lumen transition tubing shown in FIG. 29.

FIGS. 32a–c are end views of three multi-lumen transition tubes, made in accordance with the present invention, illustrating three examples of multi-lumen configurations which can be made using an extrusion die in accordance with the present invention.

FIGS. 32d–f are transverse cross-sectional views, taken across the transition portion of the three respective multi-lumen transition tubes having end views as shown in FIGS. 32a–c.

DESCRIPTION OF THE PREFERRED EMBODIMENTS

Figure 1:
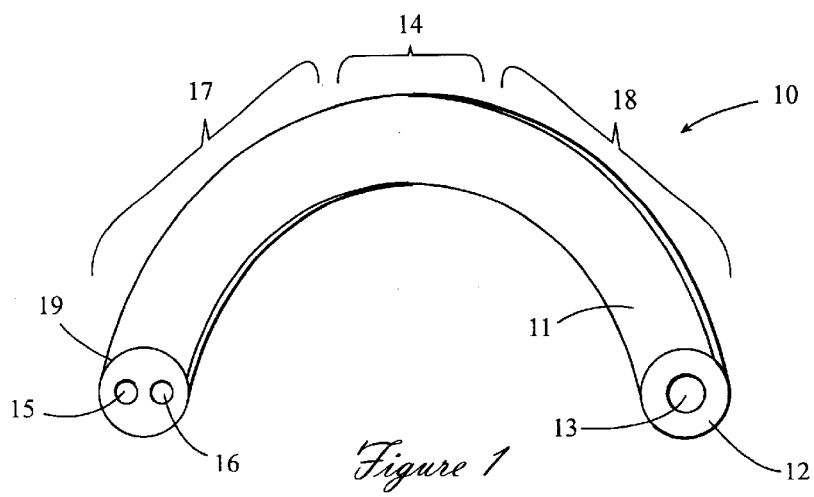
FIG. 1 is a perspective view of a length of tubing wherein one end of the tube is characterized by a single lumen therein and the opposing end by the presence of dual lumens therein and wherein the single lumen is in fluid communication with the dual lumens.

The words: "catheter" and "tube" or "tubing", are used interchangeably in the following discussion. The choice of one word rather than the others for use in a particular context should not be construed as limiting. Turning now to FIG. 1, a tube 10 is shown in perspective view. The tube 10 has an outer surface 11, a single lumen end 12 and a multilumen end 13. The tube 10 further includes a transition portion 14 disposed between the single lumen end 12 and the multilumen end 13. In FIG. 1, the multilumen end 13 is shown with two lumens 15 and 16 for the purpose of example. The segment of the tube 10 between the multilumen end 13 and the transition portion 14 is referred to hereinafter as the multilumen portion 17, whereas the segment of the tube 10 between the transition portion 14 and the single lumen end 12 is referred to as the single lumen portion 18.

Figure 2:
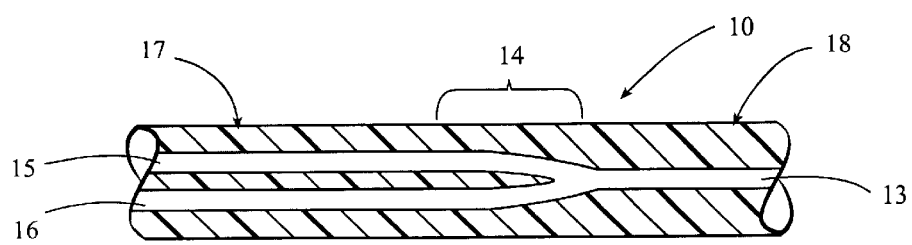
FIG. 2 is a longitudinal cross-sectional view of the transition portion of the tubing in accordance with FIG. 1 illustrating the multiple lumen-single lumen transition.

With reference now to FIG. 2, a segment of the tube 10 containing the transition portion 14 is shown in longitudinal cross-section. The single lumen the direction of which defines an axial direction, 19 bifurcates within the transition portion 14 to form a smooth union with lumens 15 and 16 comprising the multilumen portion 17 of the tube 10. The transition portion 14 is unitary is symmetric with respect to the axial direction, with both the single lumen portion 18 and the multilumen portion 17 thereby providing a unitary tube which will not separate even when the tube 10 is stretched.

Figure 3:
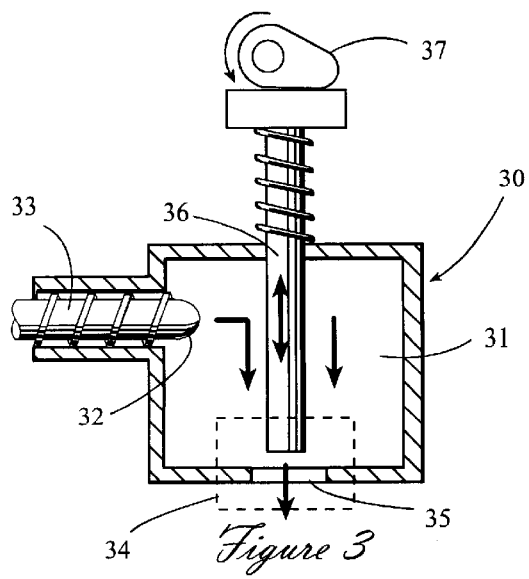
FIG. 3 is a cutaway partially cross-sectional view of an extrusion apparatus showing the axially mounted mandrel retracted from within the extruder's outlet aperture.
Figure 5:
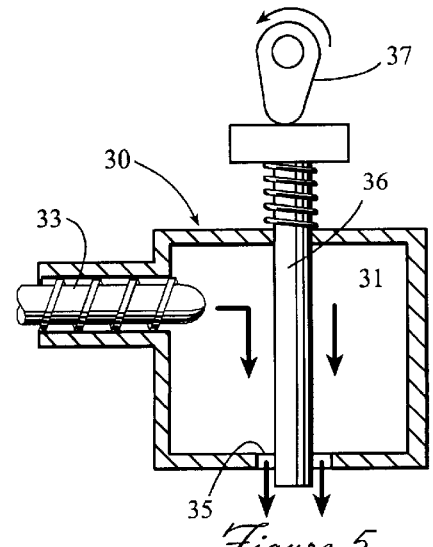
FIG. 5 is a cutaway partially cross-sectional view of an extrusion apparatus in accordance with FIG. 3, showing a lumen-forming end on the axially mounted mandrel, thrust into, and partially obstructing, the extruder's outlet aperture.

An extrusion chamber is illustrated in cross-sectional view in FIGS. 3 and 5. With reference first to FIG. 3, the extrusion chamber 30 includes a hollow interior cavity 31 having a extrudable material injection port 32 opening thereinto through which an extrudable material (not shown) is transported into the cavity 31 under pressure in the direction of the unnumbered single-headed arrows. The pressure may be provided by mechanical means, such as the auger 33 shown in FIG. 3, or by a hydraulically or pneumatically driven piston. The extrudable material (not shown) exits the cavity 31 through an extrusion die 34 to form an extruded article.

The extrusion die 34 is comprised of a die aperture 35 and a movable mandrel 36. The mandrel 36 is reciprocally driven in the direction indicated by the double-headed arrow by a programmable mandrel positioning mechanism 37 such as, for example, a cam, as shown in FIGS. 3 and 5, which may be driven by a stepper motor (not shown). Pneumatic, hydraulic and electromagnetic solenoids may also be employed for positioning the mandrel 36. When the mandrel 36 is retracted so as not to obstruct the flow of extrudable material through the die aperture 35, as shown in FIG. 3, the extruded material exits the cavity 31 through the die aperture 35 to form a rod 40 (FIG. 4) having a transverse cross-sectional shape which conforms to the shape of the die aperture.

Figure 6:
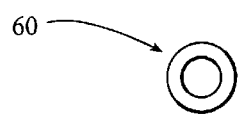
FIG. 6 is an end view of a tubular article made using the extruder shorten in FIG. 5 when the portion of the mandrel projecting within the outlet aperture has a cylindrical cross-section.

FIG. 5 illustrates, in longitudinal cross-sectional view, the extruder head 30 of FIG. 3 wherein the mandrel 36 is advanced to partially obstruct the outlet aperture 35. In this configuration, the extruded material is forced to exit the cavity 31 through the (cylindrical) space between the mandrel and the wall of the outlet aperture. In the configuration shown in FIG. 5, wherein the mandrel 36 projects within, and partially obstructs, the outlet aperture, the extruded article emerging from the outlet aperture will be a tube 60 having a transverse cross-sectional shape conforming to the corresponding shape of the outlet aperture with the mandrel therewithin as shown in FIG. 6. The shape and size of the lumen 61 is determined by the transverse cross-sectional shape and size of the portion of the mandrel within the outlet aperture.

FIGS. 7 and 8 are cross-sectional longitudinal views of a portion of an extruder head showing the mandrel and the outlet aperture in enlarged view. The mandrel 36 has a lower end 70 with a lumen forming portion 71 affixed thereto. The lumen forming portion 71 of the mandrel 36 is comprised of a single lumen forming portion 72 affixed to the lower end 70 of the mandrel 36, and a multilumen forming portion 73 rigidly affixed to the lower surface 74 of the single lumen forming portion 72. The single lumen forming portion 72 preferably has a continuous outer surface facing the wall of the outlet aperture 35. If the outlet aperture 35 is circular, and the single lumen forming portion 72 of the mandrel has a circular transverse cross-section, an article extruded through the outlet aperture 35, configured as shown in FIG. 7, will be a tube 90 (FIG. 9) having an outer diameter equal to the diameter of the outlet aperture and a circular lumen having a diameter equal to the diameter of the single lumen forming portion 72 of the mandrel.

If, during extrusion of a tubing through the extrusion die shown in FIG. 7, the mandrel 36 is retracted and repositioned such that the multilumen forming portion 73 is disposed within the outlet aperture, as shown in FIG. 8, the lumen must also change to conform to the change in shape of the opening in the outlet aperture. Thus, for example, if the multilumen forming portion 73 is comprised of a plurality of cylindrical pins 81 and 82, the extruded tubing, 100 will have a transverse cross-section as shown in FIG. 10. The multiple lumens 101 and 102 will have the same diameter as the lumen-forming pins 81 and 82 corresponding thereto. Since either the single lumen forming portion 72 and/or the multilumen forming portion 73 of the mandrel partially obstructs the flow of extrudate through the die aperture, the transition portion is formed as the mandrel changes position within the die aperture. If the repositioning occurs quickly, the transition portion of the extruded tubing will be relatively short. Conversely, when repositioning occurs slowly, the transition portion will be relatively long. FIGS. 11a–h provide some examples of multilumen configurations which can be manufactured in accordance with the present extrusion apparatus. In each embodiment of the multilumen portion of the tubing, shown in transverse cross-section in FIGS. 11a–h, the transition portion 14 of the tubing 10 provides fluid communication between the single lumen portion 18 of the extruded tubing and each and every lumen comprising the multilumen portion 17 of the tubing 10.

The die outlet aperture 35 in the extrusion chamber 30 need not be round, but may, in general, be made in any desired shape. For example, a tube 120 of unitary construction, having a oblong lumen 121 in the single lumen portion thereof, shown in transverse cross-section in FIG. 12, with the multilumen portion shown in similar sectional view in FIG. 13, can be made in a continuous process using a mandrel 36 having a lumen forming portion 73 as shown in FIG. 14; and an oblong aperture 145 having the same shape as the outer surface of the tubing 120. In addition, by completely retracting the mandrel such that no portion of the mandrel obstructs the die aperture 145, the end of the lumens can be sealed.

Figure 4:
FIG. 4 is an end view of an article extruded with the mandrel retracted from the extruder's circular outlet aperture.

The axially movable mandrel 36 may also be used for extruding a catheter having either single or multiple lumens wherein any one or all of the lumens are plugged at one or both ends of the catheter. Returning to FIG. 3 to illustrate this lumen-sealing feature, it is seen that when the mandrel 36 is retracted from the extrusion die outlet aperture 35, S the extruded article 40, shoan in end view in FIG. 4, is a solid rod. Similarly, if the lumen forming portion 73 of a mandrel comprises a plurality of lumen-reforming tines, one or all of which are slidably mounted within the mandrel, such a slidably mounted lumen-forming tine can be repositioned independently from the mandrel, to seal and/or open a lumen within the extruded tubing. For example, the mandrel, shown at 36 in FIGS. 14 and 15, can be modified such that one of the tines in the lumen forming portion 73 is mobilized, as shown in FIG. 16.

Figure 16:
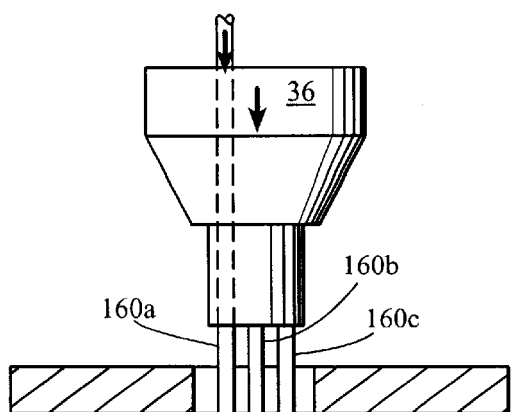
FIG. 16 is a partially cross-sectional side view of a extrusion die wherein the mandrel comprises a retractable tine on the lumen-forming portion thereof wherein the retractable tine is in an extended position.
Figure 17:
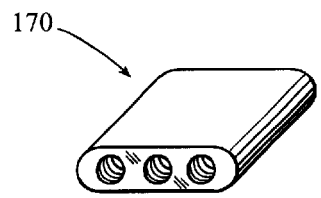
FIG. 17 is a perspective view showing the end portion of an extruded tubing exiting the outlet aperture of an extrusion die when the configuration of the mandrel and tines are in accordance with the extrusion die shown in FIG. 16.
Figure 18:
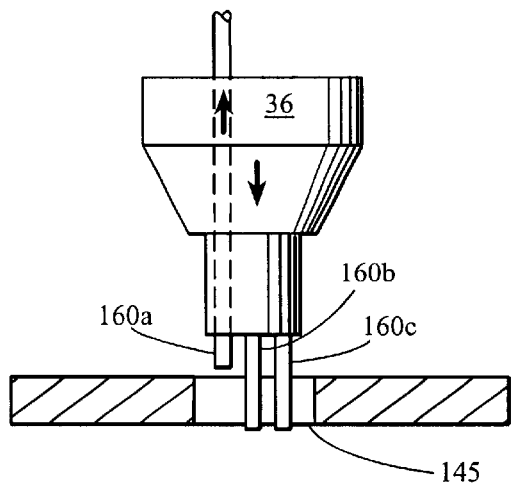
FIG. 18 is a partially cross-sectional side view of a extrusion die wherein the mandrel comprises a retractable tine on the lumen-forming portion thereof wherein the retractable tine is in a retracted position.
Figure 19:
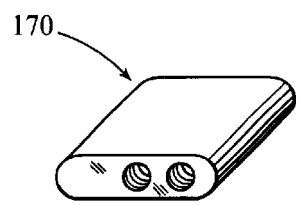
FIG. 19 is a perspective view showing the end portion of an extruded tubing exiting the outlet aperture of an extrusion die when the configuration of the mandrel and tines are in accordance with the extrusion die shown in FIG. 18.
Figure 20:
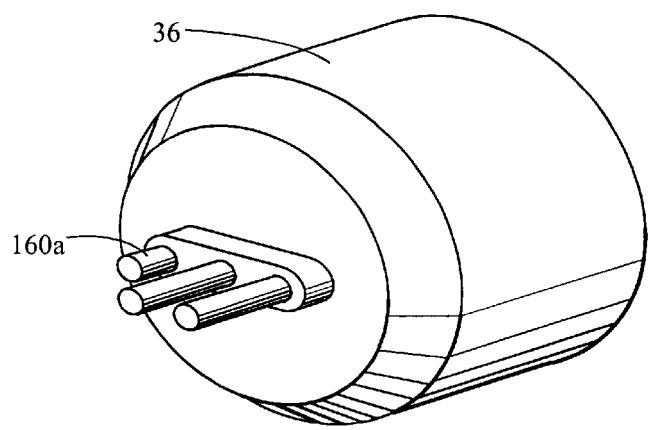
FIG. 20 is a perspective view of the mandrel shown in FIG. 18 showing the retractable tine on the lumen-forming portion of the mandrel in a retracted position.
Figure 21:
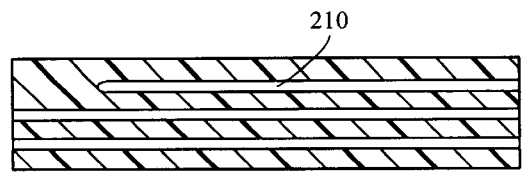
FIG. 21 is a top cross-sectional view of the unitary triple lumen portion of the extruded tubing of FIG. 19 showing termination of one of the lumens.

With reference to FIG. 16, the lumen-forming portion 73 of the mandrel 36 comprises three tines 160a–c. One of the tines is slidably mounted to move reciprocally in an axial direction (i.e. in a direction which is orthogonal to the plane defined by the die aperture which is parallel to the direction of flow of extruded material emerging from the die aperture). When both the mandrel 36 and the tine 160a are fully extended, as shown in FIG. 16, and partially occludes the die aperture 145, a tubing 170 extruded through the die aperture 145 will have a transverse geometry as shown in FIG. 17. If the movable tine 160a is retracted without moving the mandrel 36 and the stationary tines 160b and 160c, an extruded tubing emerging from the aperture 145 will have a transverse cross-section as shown in FIG. 19 wherein the lumen corresponding to tine 160a is sealed. A perspective view of the mandrel 36 of FIG. 18, with tine 160a in a retracted position, is shown in FIG. 20. FIG. 21 is a top cross-sectional view of the tubing 170 of FIG. 19 illustrating the sealed lumen 210.

Figure 22:
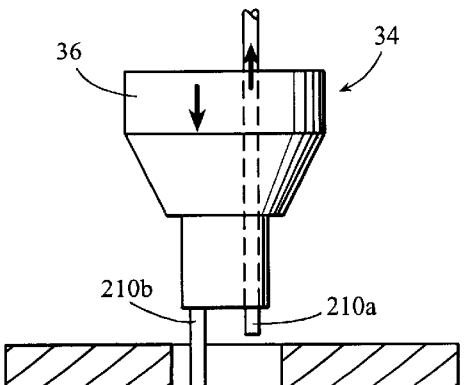
FIG. 22 is a partially cross-sectional side view of a extrusion die wherein the mandrel comprises two tines on the lumen-forming portion thereof wherein one of the two tines is retractacle and the retractable tine is in a retracted position.
Figure 23:
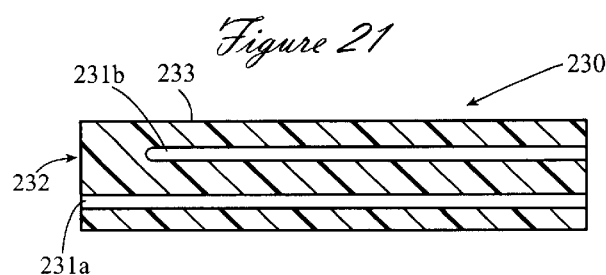
FIG. 23 is a top cross-sectional view of a unitary double lumen portion of an extruded tubing made using the mandrel/aperture configuration of FIG. 22 showing termination of only one of the two lumens.

FIG. 22 illustrates, in partial cross-section, an extrusion die 34 having a mandrel 36 which may be used to extrude a double lumen catheter 230, shown in FIG. 23. One of the lumens 231a of the dual lumen tubing 230 opens at the distal end 232 of the catheter 230 whereas the other lumen, 231b, terminates proximal to the distal end 232 of the catheter 230. If a perforation 233 is made in the side of the tube 230 adjacent to the terminus of lumen 231b, lumen 231b can be used, for example, for inflating and deflating a balloon (not shown) affixed to the outer surface of the unitary dual lumen tubing 230.

Figure 24:
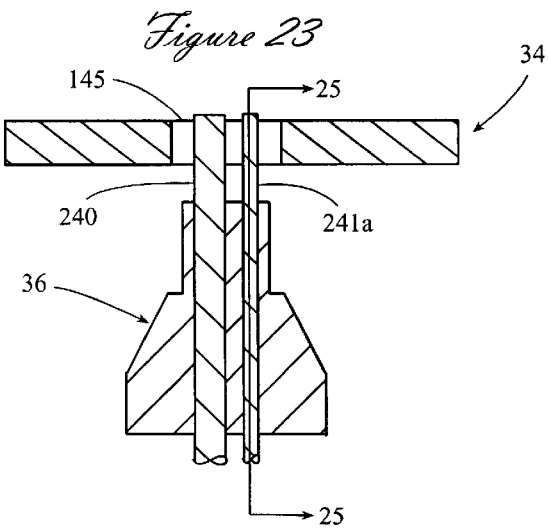
FIG. 24 is a side cross-sectional view of an extrusion die operable for extruding the triple-lumen tubing shown in FIGS. 26 and 28–31, wherein all lumen-forming tines comprising the mandrel are fully extended to partially occlude the die outlet aperture.
Figure 25:
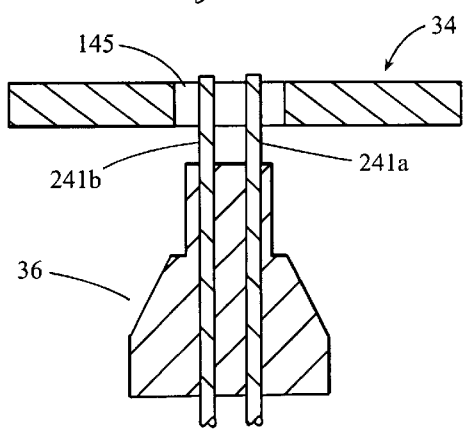
FIG. 25 is a side cross-sectional view of the extrusion die of FIG. 24 taken along section line 25—25.
Figure 27:
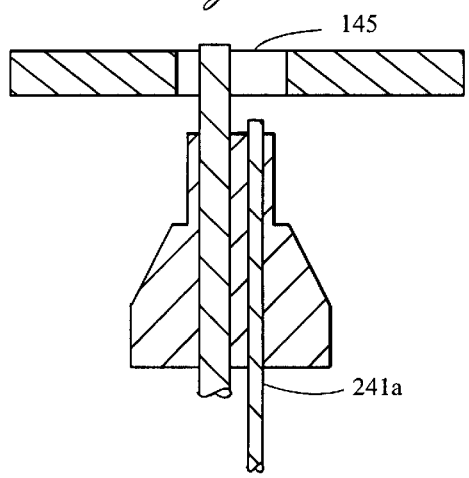
FIG. 27 is a side cross-sectional view of the extrusion die of FIG. 24, operable for extruding the triple-lumen tubing shown in FIGS. 26 and 28–31, wherein two of the three lumen-forming tines on the mandrel are retracted so that only a single lumen-forming tine partially occludes the die outlet aperture.
Figure 26:
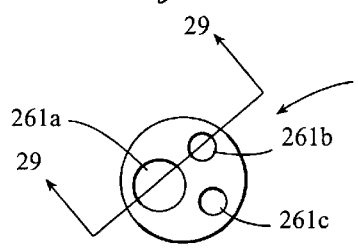
FIG. 26 is an end view of a portion of triple-lumen tubing extruded through the extrusion die shown in FIGS. 24 and 25 wherein all three lumen-forming tines on the mandrel partially occlude the die outlet aperture.

As a further example of the application of the present invention, FIGS. 24, 25 and 27 illustrate an extrusion die which may be used in cooperation with an extrusion apparatus for making a multi-lumen transition tubing wherein one or more lumens open or close in a continuous extrusion process. FIGS. 24, 25 and 27 collectively illustrate, in cross-section, an extrusion die 34 having a mandrel 36 which may be used to extrude a triple lumen catheter 260, shown in FIG. 26 and FIGS. 28–31. In FIG. 24, all three tines 240, 241a and 241b (not visible in FIG. 24) comprising the mandrel 36 extend into the die outlet aperture 145 and are flush with the uppermost surface of the outlet aperture. When the tines 140 and 141a and 141b are positioned within the die outlet aperture in accordance with FIGS. 24 and 25, a multi-lumen transition tubing 260 extruded through the die outlet aperture 145 will have a transverse lumen configuration as shown in FIG. 26. When the tines 241a and 241b are retracted to reposition the tines so as to not obstruct the die outlet aperture, as shown in FIG. 27, a multi-lumen transition tubing 260 extruded through the die outlet aperture 145 will have a lumen configuration as shown in transverse cross-section in FIG. 28. With reference to FIG. 29, lumen 261a is coextensive with the length of the triple-lumen transition tubing 260, whereas the other two lumens 261b and 261c (not visible in FIG. 29) terminate between the proximal end 291 and the distal end 292 of the catheter 260. The lumen configuration at the proximal end 291 and distal end 292 of the multi-lumen transition tubing 260 is shown in FIGS. 30 and 31 respectively. The transverse cross-section of the transition portion 14 of the tubing 260, viewed along section line 28—28, will have the lumen configuration shown in FIG. 28.

FIGS. 32a–c are exemplary, showing in end view, three of the many possible lumen configurations which may be embodied in an extruded multi-lumen tubing using an extrusion die in accordance with the present invention. FIGS. 32d–f illustrate, in cross-sectional view, the lumen configuration of the transition portion of the respective multi-lumen transition tubes shown in FIGS. 32a–c. In FIG. 32a, an end view of a multi-lumen transition tubing 320 is configured to include two lumens 321 and 322, only one of which lumens (322) is present in the transition portion as shown in FIG. 32d. Similarly, of the two lumens 323 and 324, present in the multi-lumen portion of a multi-lumen tubing 320', shown in FIG. 32b, only lumen 323 traverses the transition portion as shown in FIG. 32e. In the quadruple-lumen transition tubing 320", shown in end view in FIG. 32c, there are four lumens, 325, 326, 327 and 328, present. FIG. 32f shows that only one lumen, lumen 328, traverses the transition portion of the multi-lumen transition tubing 320".

It should now be clear that the extrusion die construction and operation, described above, can be employed to make a unitary tubing in any desired length and lumen configuration. For example, the mandrel 34 can be replaced with a plurality of mandrels adjacent to one another, any one of which may be independently repositionable. Any or all of the mandrels may, in turn, have any number of tines of any shape on the lumen-forming portions thereof. In addition, any or all of the tines may be retractably mounted within their respective mandrels. It is possible to make a unitary tubing having a first portion with m lumens therein, where m=0,1,2,3 . . . ,∞, and a second portion having n lumens therewithin, where n=1,2,3,4 . . . ,∞, with any one or all of the n lumens in fluid communication with one of the m lumens via the transition portion. It is, therefore, intended that all such embodiments of tubing and all such changes and modifications of the mandrel as required to make such multi-lumen tubing are within the scope of this invention.

With reference now to FIG. 2, the tubing 10 has a single axial lumen 19 having an elongate central axis defining an axial direction. The transition portion 14 of the tubing 10 is symmetric with respect to the axial direction. Lumens 15 and 16 converge uniformly and symmetrically to coalesce with single lumen 19. The contours of the lumen al surfaces within the transition portion 14 are smooth to prevent turbulence and minimize the possibility of clotting in the event that blood is transported across the transition portion 14. The symmetry of the lumens within the transition portion provides substantially turbulence-free flow of fluid through the transition portion. In addition, tubing made in accordance with the present invention, shown in FIGS. 1 and 2, has a uniform outer diameter along the entire length of the tubing.

In summary, a multilumen tubing having unitary construction and a method for making the tubing has been described. In one embodiment, the tubing has a single lumen portion having a first length and a single lumen therewithin The single lumen has an elongate central axis defining an axial direction, and is coextensive with the first length. The tubing also has a multiple lumen portion having a second length and at least two lumens therewithin, the two lumens being coextensive with the second length. The first lumen is in fluid communication with the two lumens comprising the multiple lumen portion through a transition portion disposed between the single lumen portion and the multiple lumen portion. The transition portion provides fluid communication between the single lumen and the two lumens comprising the multiple lumen portion. The transition portion contains fluid conducting channels therewithin that are symmetrically disposed with respect to the axial direction.

Figure 28:
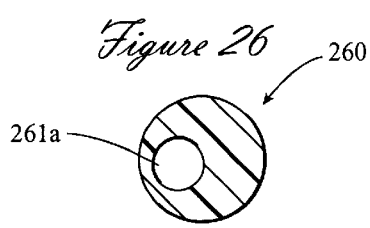
FIG. 28 is a cross-sectional view, taken along section line 28—28 of FIG. 29, of the single lumen transition portion of the triple-lumen tubing extruded through the extrusion die shown in FIGS. 24 and 25, formed when two of the three lumen-forming tines on the mandrel arc retracted so that only a single lumen-forming tine partially occludes the die outlet aperture.

In another embodiment shown in FIG. 29, and in cross-section in FIG. 28, a multilumen tubing 260 having unitary construction has a proximal end 291 and a distal end 292 and a body portion having a length therebetween. One lumen 261a is coextensive with the entire length of the body portion whereas another lumen 261b is open at one end 292 of said tubing and occluded at a point within the body portion. The occluded portion 14 does not include a plugging material but rather is unitary with the body portion and extruded therewith.

While particular embodiments of the present invention have been illustrated and described, it would be obvious to those skilled in the art that various other changes and modifications can be made without departing from the spirit and scope of the invention. For example, although medical grade silicone clastomer is a preferred extrudable material for tubing having medical applications, other extrudable materials may be preferred for other applications as a design choice. Similarly, as stated above, while the invention has been described using a tubing having a single lumen portion and a multilumen portion with a transition portion therebetween as exemplars, it is clear that bifurcation. trifurcation and further division of the mandrel, together With independently retractable or extendable tines, can be used to produce a unitary tubing having two portions spaced by a transition portion with any desired number of lumens in the two portion, the transition portion providing fluid communication between any of the lumens of the first portion with any of the lumens of the second portion. It is, therefore, intended to cover in the appended claims all such changes and modifications that are within the scope of this invention.

What we claim is:

1. A tubing having unitary construction comprising a single lumen portion having a first length and a single lumen therewithin, said single lumen having an elongate central axis defining an axial direction, said single lumen being coextensive with said first length, a multiple lumen portion having a second length and at least two lumens therewithin coextensive with said second length wherein said first lumen is in fluid communication with said two lumens comprising said multiple lumen portion, the tubing further comprising a transition portion disposed between said single lumen portion and said multiple lumen portion, said transition portion providing fluid communication between said single lumen and lumens comprising the multiple lumen portion, and wherein said transition portion contains fluid channels therewithin that are symmetrically disposed with respect to said axial direction.

2. A tubing of unitary construction having a tube length comprising a first portion having a first length and a plurality of first lumens therewithin, said plurality of first lumens being coextensive with said first length, a second portion having a second length and a second number of lumens coextensive with said second length, and a transition portion disposed between said first length and said second length wherein said second number of lumens is greater than said plurality of first lumens.

3. The tubing of unitary construction in accordance with claim 2 wherein one lumen comprising said plurality of first lumens has a central axis defining an axial direction and is in fluid communication with at least two lumens comprising said second number of lumens by means of said transition portion wherein said transition portion includes fluid conduction channels therewithin that are symmetric with respect to said axial direction.

* * * * *